US010123987B2

(12) United States Patent
Venkateshwaran et al.

(10) Patent No.: US 10,123,987 B2
(45) Date of Patent: Nov. 13, 2018

(54) TOPICAL PHARMACEUTICAL COMPOSITION OF ACITRETIN

(71) Applicant: SUN PHARMACEUTICAL INDUSTRIES LIMITED, Mumbai, Maharashtra (IN)

(72) Inventors: Rathinasabapathy Venkateshwaran, Madurai (IN); Vikas Jain, Ghaziabad (IN); Vaibhav Dubey, Sagar (IN); Sumit Madan, New Delhi (IN); Vinod Kumar Arora, Gurgaon (IN); Rajesh Rao, Deoria (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/033,676

(22) PCT Filed: Oct. 30, 2014

(86) PCT No.: PCT/IB2014/065721
§ 371 (c)(1),
(2) Date: May 2, 2016

(87) PCT Pub. No.: WO2015/063723
PCT Pub. Date: May 7, 2015

(65) Prior Publication Data
US 2016/0271092 A1    Sep. 22, 2016

(30) Foreign Application Priority Data
Oct. 31, 2013 (IN) .......................... 3231/DEL/2013

(51) Int. Cl.
*A61K 31/202* (2006.01)
*A61K 9/00* (2006.01)
(Continued)

(52) U.S. Cl.
CPC .......... *A61K 31/202* (2013.01); *A61K 9/0014* (2013.01); *A61K 9/06* (2013.01);
(Continued)

(58) Field of Classification Search
CPC ............................... A61K 31/202; A61K 9/00
See application file for complete search history.

(56) References Cited

U.S. PATENT DOCUMENTS

| 5,643,584 A | 7/1997 | Farng et al. ................. 424/401 |
| 5,914,334 A | 6/1999 | Charu ......................... 514/337 |

(Continued)

FOREIGN PATENT DOCUMENTS

| RU | 2329037 C2 | 7/2008 | |
| WO | WO 90/14833 | 12/1990 | ............. A61K 31/78 |

OTHER PUBLICATIONS

Kligman and Kligman, "The Effect on Rhino Mouse Skin of Agents which Influence Keratinization and Exfoliation," *J. Invest. Dermatol.*, 73(5pl):354-358 (1979).

(Continued)

Primary Examiner — San Ming R Hui
(74) Attorney, Agent, or Firm — Goodwin Procter LLP

(57) ABSTRACT

The present invention relates to a topical pharmaceutical composition comprising acitretin and a process for its preparation. It also relates to a method of treating skin disorders by administering said topical pharmaceutical composition.

26 Claims, 2 Drawing Sheets

Mean Utriculi Size after Application of Various Strengths of Acitretin Gels and Tazorac® (Tazarotene) Gel

(51) Int. Cl.
  *A61K 47/10* (2017.01)
  *A61K 9/06* (2006.01)
  *A61K 47/32* (2006.01)
  *A61K 47/22* (2006.01)
  *A61K 47/26* (2006.01)

(52) U.S. Cl.
  CPC .............. *A61K 47/10* (2013.01); *A61K 47/22* (2013.01); *A61K 47/26* (2013.01); *A61K 47/32* (2013.01)

(56) References Cited

U.S. PATENT DOCUMENTS

| | | | |
|---|---|---|---|
| 6,258,830 B1 | 7/2001 | Charu | 514/337 |
| 6,353,029 B1 | 3/2002 | Parab | 514/725 |
| 2013/0089575 A1* | 4/2013 | Surman | A61K 31/202 424/400 |
| 2013/0184243 A1* | 7/2013 | Alonso | A61K 31/131 514/171 |

OTHER PUBLICATIONS

Hsia et al., "Effects of Topically Applied Acitretin in Reconstructed Human Epidermis and the Rhino Mouse," *J. Invest. Dermatol.*, 128(1):125-130 (2008).

Agrawal et al., "Development, evaluation and clinical studies of Acitretin loaded nanostructured lipid carriers for topical treatment of psoriasis," *International Journal of Pharmaceutics*, 401(1-2):93-102 (2010).

Office Action dated Apr. 24, 2018 for CA Patent Application No. 2,929,292.

Office Action of the Federal Institute of Industrial Property (FIPS) for Application No. 2016117298/15 filed Oct. 30, 2014.

\* cited by examiner

Figure 1: Mean Utriculi Size after Application of Various Strengths of Acitretin Gels and Tazorac® (Tazarotene) Gel
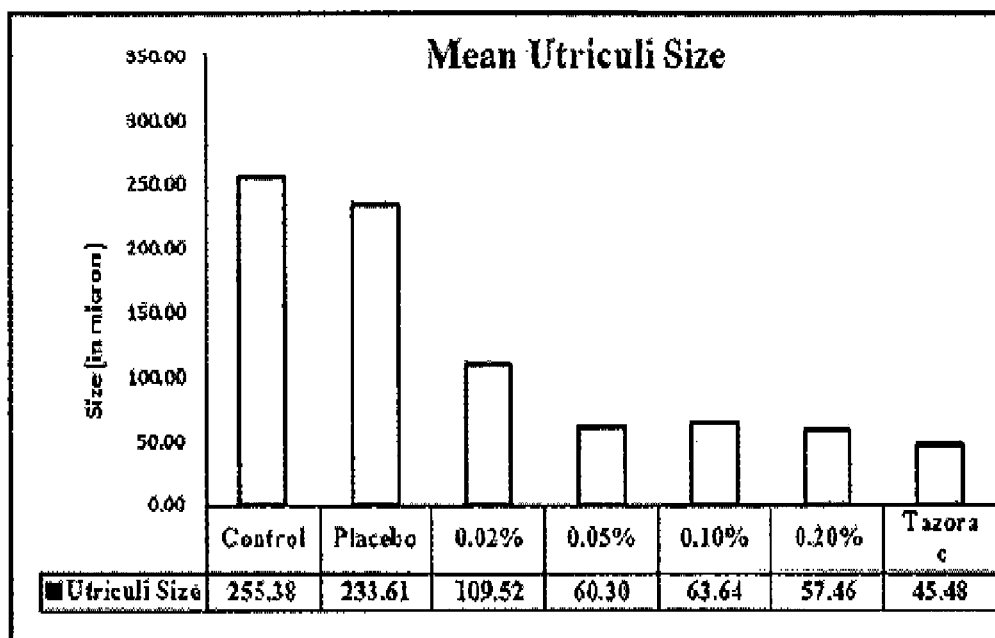

Figure 2: Percentage Reduction in Utriculi Size After Application of Various Strengths of Acitretin Gels and Tazorac® (Tazarotene) Gel With Respect to Control
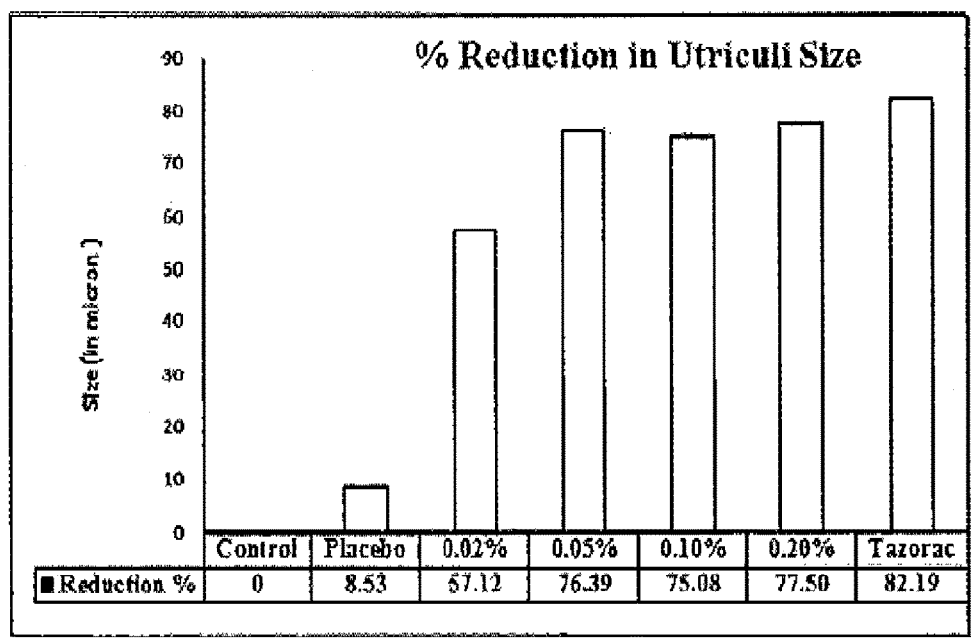

TOPICAL PHARMACEUTICAL COMPOSITION OF ACITRETIN

FIELD OF THE INVENTION

The present invention relates to a topical pharmaceutical composition comprising acitretin and a process for its preparation. It also relates to a method of treating skin disorders by administering said topical pharmaceutical composition.

BACKGROUND OF THE INVENTION

Psoriasis is a chronic, non-contagious skin disorder. It appears in many different forms and can affect any part of the body.

Currently, there is no cure for psoriasis. However, over the years a wide variety of topical and systemic treatment methods that inhibit the inflammation, cell proliferation, or cell differentiation have been developed. Treatment of psoriasis remains a challenge because of its chronic recurrent nature. Various topical and systemic therapies include anti-inflammatory agents, e.g., glucocorticoids; analgesics; chemically synthesized disease-modifying antirheumatic drugs (DMARDs), e.g., methotrexate and ciclosporin; anti-proliferative agents, e.g., retinoids and vitamin D analogs; TNF-α blockers, e.g., etanercept, infliximab, adalimumab, and efalizumab; monoclonal antibodies against B cells, e.g., rituximab; T-cell activation blockers, e.g., abatacept; IL-1 blockers, e.g., anakinra; coal tar; and phototherapy.

These treatment methods have proven to be of limited value due to disadvantages such as cosmetic liabilities, severe side effects, high cost, and minimal or short-term efficacy.

Retinoids, as an alternative, are also known to influence keratinocyte differentiation and have proven to be effective in the treatment of a variety of keratinization disorders including psoriasis.

U.S. Pat. No. 6,353,029 discloses a topical solution composition comprising tretinoin, 4-hydroxy anisole, polyethylene glycol, an antioxidant, a chelating agent, a lower alkanol, and water.

U.S. Pat. No. 5,643,584 discloses a topical aqueous gel composition comprising unsolubilized micronized tretinoin particles, a surfactant selected from the group consisting of octoxynol and nonoxynol, a preservative, a gelling agent, and water.

PCT Publication No. WO 90/14833 discloses an aqueous gel vehicle for topical application to the skin comprising active ingredients such as retinoids, in particular tretinoin. The composition also includes an aqueous medium, a gelling agent, and an antioxidant.

U.S. Pat. Nos. 5,914,334 and 6,258,830 disclose topical gel compositions of tazarotene comprising poloxamer 407, polysorbate 40, and hexylene glycol for the treatment of acne and psoriasis.

A review of the prior art thus reveals topical pharmaceutical compositions of retinoids such as tretinoin and tazarotene for the treatment of skin disorders such as psoriasis. However, irritancy to the skin remains the common side effect, leading to a high level of patient non-compliance.

Acitretin, a metabolite of etretinate, is available as an oral capsule dosage form and is indicated for the treatment of severe psoriasis. As the use of acitretin is limited by its systemic side effects, and skin being the target organ for the treatment of psoriasis, there remains an unmet need for topical pharmaceutical compositions of acitretin with minimal or no systemic side effects and with reduced irritancy to the skin.

For a topical pharmaceutical composition, the solubilization and release of a drug from the composition remain the essential prerequisites to ensure effective treatment. As acitretin is poorly soluble in water, it remains a great challenge to develop a topical pharmaceutical composition in which acitretin is maximally solubilized and readily released from the composition into the skin.

The scientists of the present invention have now developed a topical pharmaceutical composition of acitretin with an acceptable level of efficacy for treating psoriasis and with reduced irritancy. Further, acitretin is found to be readily released from the composition into the skin. Also, said composition of the present invention is found to be stable.

SUMMARY OF THE INVENTION

The topical pharmaceutical composition of the present invention is a significant advance over the currently available oral dosage form of acitretin, as there are minimal or no systemic side effects. Further, the topical pharmaceutical composition of acitretin results in better patient compliance in comparison to the available oral dosage form. In particular, the topical pharmaceutical composition of acitretin is in the form of a gel and is found to be stable for at least three months.

The present invention relates to a topical pharmaceutical composition comprising acitretin and a process for its preparation. It also relates to a method of treating a skin disorder by administering said topical pharmaceutical composition.

BRIEF DESCRIPTION OF THE DRAWINGS

FIG. 1 is a bar chart presentation of mean utriculi size after application of various strengths of acitretin gels and Tazorac® (tazarotene) gel.

FIG. 2 is a bar chart presentation of percentage reduction in utriculi size after application of various strengths of acitretin gels and Tazorac® (tazarotene) gel with respect to control.

DETAILED DESCRIPTION OF THE INVENTION

A first aspect of the present invention provides a stable topical pharmaceutical composition of acitretin comprising a therapeutically effective amount of acitretin and one or more gelling agents.

According to one embodiment of this aspect, the percentage of gelling agent ranges from about 0.05% w/w to about 10% w/w of the composition.

According to another embodiment of this aspect, the gelling agent is a carboxyvinyl polymer.

According to another embodiment of this aspect, the topical pharmaceutical composition consists essentially of acitretin as the active ingredient, one or more gelling agents to form a gel, a solvent in which to disperse the gelling agent, and a co-solvent in which to dissolve the acitretin. Combining the one or more gelling agents and solvent for dispersing the gelling agent with the solution of acitretin/co-solvent provides a gel of acitretin suitable for topical administration.

The topical pharmaceutical composition may consist essentially of one or more gelling agents being present at a percentage ranging from about 0.05% w/w to about 10% w/w based on the total weight of the composition, one or more solvents to disperse the one or more gelling agents, the acitretin present in an amount of about 0.02% w/w to about 5% w/w based on the total weight of the composition, and one or more co-solvents to dissolve the acitretin.

According to another embodiment of this aspect, the topical pharmaceutical composition consists of acitretin as the sole active ingredient, one or more gelling agents to form a gel, a solvent in which to disperse the gelling agent, and a co-solvent in which to dissolve the acitretin. Combining the one or more gelling agents and solvent for dispersing the gelling agent with the solution of acitretin/co-solvent provides a gel of acitretin suitable for topical administration.

In one embodiment, the topical pharmaceutical compositions disclosed herein are characterized as being unencapsulated.

A second aspect of the present invention provides a stable topical pharmaceutical composition comprising more than about 0.05% w/w ofacitretin, wherein the composition has a mean in-vitro release rate of more than about 10.00 µg/cm$^2$/h$^{1/2}$ as measured using a Franz diffusion cell with the conditions of receptor solution comprising isopropyl alcohol and water (60:40, v/v), the membrane a Supor® 200, dosage 300±30 mg, temperature 32° C.±1.0° C.

A third aspect of the present invention provides a process for the preparation of a stable topical pharmaceutical composition of acitretin, wherein the process comprises the steps of:

(i) dispersing one or more gelling agents in a suitable solvent;
(ii) dispersing/dissolving acitretin and one or more pharmaceutically acceptable excipients in a suitable co-solvent; and
(iii) mixing the dispersion of step (i) with the dispersion/solution of step (ii) to form a gel.

A fourth aspect of the present invention provides a method of treating a skin disorder by administering a stable topical pharmaceutical composition of acitretin comprising a therapeutically effective amount of acitretin and one or more gelling agents.

According to one embodiment of this aspect, the skin disorder is selected from the group comprising psoriasis, keratosis, eczema, rosacea, acne vulgaris, dermatitis, pruritus, seborrhea, skin cancers, inflammation, other skin disorders which are responsive to acitretin or etretinate, and combinations thereof.

According to another embodiment of this aspect, the skin disorder is psoriasis.

According to another embodiment of this aspect, the skin disorder is keratosis.

The term "topical," as used herein, refers to a composition meant for application to the skin, nail, or mucosal tissue.

The term "therapeutically effective amount," as used herein, refers to an amount effective at dosages and for periods of time necessary to achieve the desired result of treating skin disorders, in particular psoriasis and keratosis.

The term "pharmaceutical composition," as used herein, refers to gels, solutions, suspensions, foams, lotions, or sprays. In particular, the pharmaceutical composition of the present invention is a gel.

The term "acitretin," as used herein, refers to all-trans-9-(4-methoxy-2,3,6-trimethylphenyl)-3,7-dimethyl-2,4,6,8-nonatetraenoic acid. It further includes its salts, polymorphs, hydrates, solvates, prodrugs, chelates, or complexes. The topical pharmaceutical composition of the present invention comprises acitretin in an amount from about 0.005% w/w to about 10% w/w, in particular from about 0.02% w/w to about 5% w/w based on total weight of the composition.

The term "about," as used herein, refers to any value which lies within the range defined by a variation of up to ±10% of the value.

The term "stable," as used herein, means not more than 10% w/w of total related substances are formed on storage at a temperature of 40° C. and a relative humidity of 75% or at a temperature of 25° C. and a relative humidity of 60%, for a period of at least three months to the extent necessary for the sale and use of the composition without substantial change in the mean in-vitro release rate of acitretin from the composition. The mean in-vitro release rate of acitretin from the topical pharmaceutical compositions of the present invention upon storage at 40° C./75% relative humidity (RH) for at least three months is substantially similar to the initial mean in-vitro release rate of acitretin obtained as soon as practicable after preparation of topical pharmaceutical compositions.

The term "substantial," as used herein, refers to any value which lies within the range defined by a variation of up to ±20% of the value.

The term "gelling agent," as used herein, refers to an agent which forms a gel when added to a suitable solvent. Suitable gelling agents are selected from the group comprising carboxyvinyl polymers, e.g., Carbopol® 980, Carbopol® 974P, Carbopol® 971P, and Carbopol® 934P; natural gums, e.g., karaya gum, locust bean gum, guar gum, xanthan gum, arabic gum, tragacanth gum, carrageenan, pectin, agar, alginic acid, and sodium alginate; cellulose derivatives, e.g., hydroxypropyl methyl cellulose, hydroxypropyl cellulose, methylcellulose, hydroxyethyl cellulose, and sodium carboxymethylcellulose; acrylates, e.g., methacrylates and polyacrylates; alginic acid-propylene glycol esters; polyoxyethylene-polyoxypropylene copolymers; polyvinyl pyrrolidone; polyethylene glycol; polyethylene oxide; polyvinyl alcohol; silicon dioxide; and mixtures thereof. In particular, the gelling agent used in the topical pharmaceutical composition of the present invention is a carboxyvinyl polymer. The topical pharmaceutical composition of the present invention comprises a gelling agent in an amount of from about 0.05% w/w to about 10% w/w, in particular from about 0.1% w/w to about 5% w/w, based on total weight of the composition.

Acitretin being poorly insoluble in water, a plurality of non-aqueous vehicles as co-solvents has been used in the present invention to solubilize acitretin. The term "co-solvent," as used herein, refers to an organic solvent which is used to disperse or dissolve acitretin. Suitable co-solvents are selected from the group comprising ethers, e.g., diethylene glycol monoethyl ether; glycols, e.g., propylene glycol, polyethylene glycol, and glycerin; dimethyl isosorbide; fatty acid esters, e.g., isopropyl myristate, isopropyl palmitate, isopropyl stearate, and ethyl oleate; fatty acids, e.g., capric acid, lauric acid, myristic acid, oleic acid, and linoleic acid; polyoxyethylene sorbitan esters, e.g., polysorbate 20, polysorbate 40, polysorbate 60, and polysorbate 80; and mixtures thereof. Certain water-miscible solvents, e.g., glycerin or propylene glycol, also add beneficial humectant properties to the composition. The amount of co-solvent used in the present invention ranges from about 15% w/w to about 45% w/w, more preferably from about 20% w/w to about 30% w/w based on the total weight of the composition. In the present invention, the total amount of acitretin may be present as solubilized acitretin fraction and remaining as unsolubilized acitretin fraction.

The selection of co-solvents remains an important factor as it determines the solubility and release of acitretin from the composition. In a preferred embodiment, the co-solvent is a combination of diethylene glycol monoethyl ether present in a range of about 20% w/w to about 30% w/w, dimethyl isosorbide present in a range of about 1% w/w to about 10% w/w, and polysorbate 80 present in a range of about 0.1% w/w to about 5% w/w, based on total weight of the composition. The solubility of acitretin increases to approximately 10,000 times in comparison to solubility in water, when dimethyl isosorbide, diethylene glycol monoethyl ether, and polysorbate 80 are used in a w/w ratio of about 3.3:24.1:1. Besides increasing the solubility to a remarkable level, the combination of these co-solvents also helps to provide the desirable release of acitretin from the composition into the skin.

The term "solvent," as used herein, refers to a vehicle used to disperse or dissolve one or more gelling agents. Suitable solvents are selected from the group comprising water, white soft paraffin, light liquid paraffin, heavy liquid paraffin, mineral oil, hydrocarbon oil, ester oil, triglyceride oil, oil of plant origin, oil of animal origin, unsaturated or polyunsaturated oil, essential oil, silicone oil, and mixtures thereof. In particular, the solvent used in the topical pharmaceutical composition of the present invention is water.

The topical pharmaceutical composition of the present invention further comprises one or more pharmaceutically acceptable excipients selected from the group comprising percutaneous absorption enhancers, antioxidants, preservatives, chelating agents, surfactants, pH-adjusting agents, humectants, fragrances, and mixtures thereof.

Suitable percutaneous absorption enhancers are selected from the group comprising sulfoxides, e.g., dimethyl sulfoxide (DMSO); ethers, e.g., diethylene glycol monoethyl ether (Transcutol®); surfactants, e.g., sodium laurate, sodium lauryl sulfate, polysorbate 20, polysorbate 40, polysorbate 60, and polysorbate 80; alkyl glycosides; alcohols, e.g., ethanol, propanol, and benzyl alcohol; fatty acids, e.g., lauric acid, oleic acid, valeric acid, and isostearic acid; fatty acid esters, e.g., isopropyl myristate and isopropyl palmitate; polyols or esters thereof, e.g., propylene glycol, ethylene glycol, glycerol, butanediol, and polyethylene glycol; amides or other nitrogenous compounds, e.g., urea, dimethyl acetamide, dimethyl formamide, 2-pyrrolidone, 1-methyl-2-pyrrolidone, ethanolamine, diethanolamine, and triethanolamine; terpenes; dimethyl isosorbide; alkanones; and mixtures thereof.

Suitable antioxidants are selected from the group comprising butylated hydroxy anisole, butylated hydroxy toluene, sodium metabisulfite, ascorbic acid, ascorbyl palmitate, thiourea, acetylcysteine, dithiothreitol, cysteine hydrochloride, propyl gallate, tert-butyl hydroquinone, beta-carotene, tocopherols, and mixtures thereof.

Suitable preservatives are selected from the group comprising methyl-, ethyl-, propyl-, or butyl-esters of hydroxy benzoic acid or sodium salts thereof, benzoic acid, sodium benzoate, chlorhexedine, benzalkonium chloride, 2-phenoxyethanol, cetrimide, potassium sorbate, imidurea, dichlorobenzyl alcohol, thiomersal, and mixtures thereof.

Suitable chelating agents are selected from the group comprising ethylenediamine tetraacetic acid or derivatives or salts thereof, e.g., disodium edetate; dihydroxyethyl glycine; glucamine; acids, e.g., citric acid, tartaric acid, gluconic acid, and phosphoric acid; and mixtures thereof.

Suitable surfactants are selected from the group comprising polyethoxylated fatty acid esters, polyoxyethylene sorbitan esters, polyoxyethylene hydrogenated castor oil, polyoxyethylene polyoxypropylene glycol, sorbitan esters, sodium lauryl sulphate, docusate sodium, nonooxynol, glyceryl monostearate, and mixtures thereof.

Suitable pH-adjusting agents are selected from the group comprising organic or inorganic acids, e.g., citric acid, acetic acid, fumaric acid, tartaric acid, phosphoric acid, and hydrochloric acid; organic or inorganic bases, e.g., sodium hydroxide, potassium hydroxide, ammonium hydroxide, and triethanolamine; and buffers, e.g., phosphate buffers and acetate buffers. The pH of the topical pharmaceutical composition of the present invention is adjusted from about 4 to about 7.

Suitable humectants are selected from the group comprising propylene glycol, glycerin, butylene glycol, sorbitol, triacetin, and mixtures thereof.

Examples of fragrances that may be used in the composition include lavender oil, rose oil, lemon oil, almond oil, other FDA-approved fragrances, and mixtures thereof.

The compositions of the present invention may further comprise an auxiliary agent, which may act as a cooling agent. Suitable cooling agents are selected from the group comprising menthol, e.g., l-menthol and dl-menthol; camphor, e.g., d-camphor and dl-camphor; borneol, e.g., d-borneol and dl-borneol; and mixtures thereof. Plant oils and extracts containing one or more of these compounds, e.g., peppermint oil, peppermint extract, camphor tree extract, and lavender extract, may also be used.

The following examples represent various embodiments according to the present invention. The examples are given solely for the purpose of illustration and are not to be construed as limitations of the present invention, as many variations thereof are possible without departing from the spirit and scope of the invention.

EXAMPLES

Example 1

| Ingredients | Quantity (% w/w) |
| --- | --- |
| Acitretin | 0.20 |
| Diethylene glycol monoethyl ether | 24.20 |
| Dimethyl isosorbide | 3.33 |
| Butylated hydroxy anisole | 0.05 |
| Carbopol ® 980 | 0.50 |
| Sodium hydroxide solution | q.s. |
| Purified water | q.s. to 100.00 |

Procedure:
1. Carbopol® 980 was dispersed in purified water under stirring.
2. Acitretin, butylated hydroxy anisole, and dimethyl isosorbide were added into diethylene glycol monoethyl ether and mixed together.
3. The mixture of step 2 was added into the dispersion of step 1 under stirring.
4. Purified water was added into the dispersion of step 3 to achieve the desired weight.
5. The pH of the dispersion of step 4 was adjusted to 5 to 6 using sodium hydroxide solution to form a gel.

Example 2

| Ingredients | Quantity (% w/w) |
| --- | --- |
| Acitretin | 0.20 |
| Diethylene glycol monoethyl ether | 24.10 |
| Dimethyl isosorbide | 3.30 |
| Polysorbate 80 | 1.00 |
| Ascorbic acid | 0.05 |
| Butylated hydroxy anisole | 0.05 |
| Disodium edetate | 0.10 |
| Sodium benzoate | 0.20 |
| Carbopol ® 980 | 1.25 |
| Sodium hydroxide solution | q.s. |
| Purified water | q.s. to 100.00 |

Procedure:
1. Carbopol® 980 was dispersed in purified water under stirring.
2. Acitretin, butylated hydroxy anisole, dimethyl isosorbide, and polysorbate 80 were added into diethylene glycol monoethyl ether and mixed together.
3. Disodium edetate, sodium benzoate, and ascorbic acid were dissolved into purified water.
4. The mixture of step 2 was added into the dispersion of step 1.
5. The mixture of step 3 was added into the dispersion of step 4.
6. Purified water was added into the dispersion of step 5 to achieve the desired weight.
7. The pH of the dispersion of step 6 was adjusted to 5 to 6 using sodium hydroxide solution to form a gel.

Examples 3-7

| | Quantity (% w/w) | | | | |
|---|---|---|---|---|---|
| Ingredients | Example 3 | Example 4 | Example 5 | Example 6 | Example 7 |
| Acitretin | 0.02 | 0.05 | 0.10 | 0.15 | 0.25 |
| Diethylene glycol monoethyl ether | 24.10 | 24.10 | 24.10 | 24.10 | 24.10 |
| Dimethyl isosorbide | 3.30 | 3.30 | 3.30 | 3.30 | 3.30 |
| Polysorbate 80 | 1.00 | 1.00 | 1.00 | 1.00 | 1.00 |
| Butylated hydroxy anisole | 0.05 | 0.05 | 0.05 | 0.05 | 0.05 |
| Carbopol ® 980 | 1.25 | 1.25 | 1.25 | 1.25 | 1.25 |
| Disodium edetate | 0.10 | 0.10 | 0.10 | 0.10 | 0.10 |
| Sodium benzoate | 0.20 | 0.20 | 0.20 | 0.20 | 0.20 |
| Ascorbic acid | 0.05 | 0.05 | 0.05 | 0.05 | 0.05 |
| Sodium hydroxide solution | q.s. | q.s. | q.s. | q.s. | q.s. |
| Purified water | q.s. to 100.00 | q.s. to 100.00 | q.s. to 100.00 | q.s. to 100.00 | q.s. to 100.00 |

Examples 8-13

Procedure:
1. Carbopol® 980 was dispersed in purified water under stirring.
2. Acitretin, butylated hydroxy anisole, dimethyl isosorbide, and polysorbate 80 were added into diethylene glycol monoethyl ether and mixed together.
3. Disodium edetate, sodium benzoate, and ascorbic acid were dissolved into purified water.
4. The mixture of step 2 was added into the dispersion of step 1.
5. The mixture of step 3 was added into the dispersion of step 4.
6. Purified water was added into the dispersion of step 5 to achieve the desired weight.
5. The pH of the dispersion of step 6 was adjusted to 5 to 6 using sodium hydroxide solution to form a gel.

Solubility Studies

The saturation solubility of acitretin was determined by adding an excess amount of acitretin in a conical flask containing a mixture of dimethyl isosorbide, diethylene glycol monoethyl ether, and polysorbate 80, present in a w/w ratio of 3.3:24.1:1. The mixture was kept in a shaking water bath for 24 hours at 25° C. The saturation solubility of acitretin was measured to be 2.5 mg/mL by HPLC method [YIN/IC-Pack® ODS-A column C-18 (150×4.6 mm, 5 μm); mobile phase of methanol:ethanol:glacial acetic acid:water (74:21:5:0.5 v/v/v/v); flow rate of 1.5 mL/min; UV detection at 360 nm].

The solubility of acitretin was found to be 0.7025 mg/g of the gel in given compositions of Examples 5 through 10 containing 0.284 g of a mixture of dimethyl isosorbide, diethylene glycol monoethyl ether, and polysorbate 80, present in a w/w ratio of 3.3:24.1:1. Table 1 gives the percentage of the acitretin in a solubilized form in acitretin gels prepared as per Examples 2 through 9.

| | Quantity (% w/w) | | | | | |
|---|---|---|---|---|---|---|
| Ingredients | Example 8 | Example 9 | Example 10 | Example 11 | Example 12 | Example 13 |
| Acitretin | 0.30 | 0.40 | 1.00 | 0.02 | 0.05 | 0.10 |
| Diethylene glycol monoethyl ether | 24.10 | 24.10 | 24.10 | 24.28 | 24.25 | 24.20 |
| Dimethyl isosorbide | 3.30 | 3.30 | 3.30 | 3.30 | 3.30 | 3.30 |
| Polysorbate 80 | 1.00 | 1.00 | 1.00 | 1.00 | 1.00 | 1.00 |
| Butylated hydroxy anisole | 0.05 | 0.05 | 0.05 | 0.05 | 0.05 | 0.05 |
| Carbopol ® 980 | 1.25 | 1.25 | 1.25 | 1.25 | 1.25 | 1.25 |
| Disodium edetate | 0.10 | 0.10 | 0.10 | 0.10 | 0.10 | 0.10 |
| Sodium benzoate | 0.20 | 0.20 | 0.20 | 0.20 | 0.20 | 0.20 |
| Ascorbic acid | 0.05 | 0.05 | 0.05 | 0.05 | 0.05 | 0.05 |
| Sodium hydroxide solution | q.s. | q.s. | q.s. | q.s. | q.s. | q.s. |
| Purified water | q.s. to 100.00 | q.s. to 100.00 | q.s. to 100.00 | q.s. to 100.00 | q.s. to 100.00 | q.s. to 100.00 |

TABLE 1

Percentage of Acitretin Solubilized in Acitretin
Gels Prepared as per Examples 2-9

| Example | Percentage of Acitretin Solubilized |
|---|---|
| 2 | 35.13 |
| 3 | 100.00 |
| 4 | 100.00 |
| 5 | 70.25 |
| 6 | 46.83 |
| 7 | 28.10 |
| 8 | 23.42 |
| 9 | 17.56 |

Stability Data

The gels prepared according to Example 1, Example 2, Example 11, Example 12, and Example 13 were stored at a temperature of 40° C. and a relative humidity of 75% RH for a period of three to six months, and analyzed for acitretin contents by HPLC method [YMC-Pack® ODS-A column C-18 (150×4.6 mm, 5 μm); mobile phase of methanol: ethanol:glacial acetic acid:water (74:21:5:0.5 v/v/v/v); flow rate of 1.5 mL/min; UV detection at 360 nm]. The results of the analysis are represented in Tables 2-4.

TABLE 2

Results of the Stability Study of the
Gel Prepared According to Example 1

| Conditions (40° C./75% RH) | Assay (%) | Related Substances (% w/w) |
|---|---|---|
| Initial | 101.2 | 0.14 |
| 3 Months | 102.6 | 0.13 |

TABLE 3

Results of the Stability Study of the
Gel Prepared According to Example 2

| Conditions (40° C./75% RH) | Assay (%) | Related Substances (% w/w) |
|---|---|---|
| Initial | 96.6 | 0.17 |
| 3 Months | 100.0 | 0.18 |
| 6 Months | 100.5 | 0.44 |

TABLE 4

Results of the Stability Study of the Gel
Prepared According to Examples 11-13

| Example | Conditions (40° C./75% RH) | Assay (%) | Related substances (% w/w) |
|---|---|---|---|
| 11 | Initial | 101.9 | 0.54 |
|  | 3 Months | 103.8 | 0.64 |
|  | 6 Months | 103.7 | 1.03 |
| 12 | Initial | 97.3 | 0.23 |
|  | 3 Months | 100.0 | 0.32 |
|  | 6 Months | 101.7 | 0.73 |
| 13 | Initial | 97.3 | 0.19 |
|  | 3 Months | 98.7 | 0.20 |
|  | 6 Months | 101.4 | 0.48 |

In-Vitro Release Data

An in-vitro release test was performed using a Franz diffusion cell having six individual cells and a Supor® 200 membrane. The receptor solution used was isopropyl alcohol and water (60:40, v/v). 300 Mg of the gels prepared according to Examples 2 and 5-9 were placed uniformly on the membrane at a temperature of 32° C.±1.0° C. The amount of acitretin released was determined using an HPLC method [Zorbax® column C-18 (150×4.6 mm, 5 μm); mobile phase of buffer:methanol (10:90 v/v); buffer of 20 mM ammonium acetate:acetic acid (1000:30 v/v); flow rate of 0.750 mL/min] and was analyzed using a UV detector at 350 nm. The mean acitretin release rate at 0 days, 3 months, and 6 months at 40° C./75% RH from gels prepared as per Example 2 and 5-9 is given in Table 5.

TABLE 5

Mean In-vitro Release Rate of Acitretin
Gels Prepared as per Examples 2 and 5-9

| | Mean Release Rate ($\mu g/cm^2/h^{1/2}$) | | |
|---|---|---|---|
| Example | Initial (Control) | 3 Months (40° C./75% RH) | 6 Months (40° C./75% RH) |
| 2 | 26.16 | 25.87 | 24.90 |
| 5 | 15.90 | 17.26 | 15.66 |
| 6 | 19.28 | 15.94 | 15.92 |
| 7 | 19.87 | 15.94 | 18.70 |
| 8 | 23.04 | 21.50 | 20.35 |
| 9 | 28.51 | 25.01 | 24.24 |

From the above table, it is clear that the mean in-vitro release rate of acitretin upon storage at 40° C./75% RH after 6 months is substantially similar to the initial mean in-vitro release rate from the control batches.

Rhino Mouse Test
Efficacy Studies

Rhino mouse utriculi reduction assay is a well-characterized animal model for the evaluation of retinoid activity (Kligman and Kligman, "The Effect on Rhino Mouse Skin of Agents which Influence Keratinization and Exfoliation," *J. Invest. Dermatol.*, 73(5pl):354-358, 1979) Rhino mouse skin is characterized by the presence of keratin-containing utricles attached to the epidermis. The utricle size reduction in rhino mouse can be used to determine the efficacy of a composition for the treatment of psoriasis (Hsia et al., "Effects of Topically Applied Acitretin in Reconstructed Human Epidermis and the Rhino Mouse," *J. Invest. Dermatol.*, 128(1):125-130, 2008). Acitretin gels of the present invention are compared with commercially available Tazorac® (tazarotene) gel 0.10% w/w indicated for the treatment of psoriasis.

Seven groups were made, each consisting of seven animals as described in Table 6. An amount of 100 mg±2% of placebo for acitretin gel, acitretin gels of various strengths, and reference Tazorac® (tazarotene) gel 0.10% w/w was applied evenly on the entire dorsal trunk of the animals with a sterilized spatula/glass rod daily for 14 consecutive days. All the animals from Group I to Group VII were examined for detailed clinical signs once daily during treatment and during the treatment-free period.

TABLE 6

Study Design for Acitretin Gel for Rhino Mouse Test

| Groups | Formulation/Treatment Details | Concentration (% w/w) | Animal Numbers & Sex |
|---|---|---|---|
| I | Control | — | 1-7 (5 males, 2 females) |
| II | Placebo for acitretin gel | — | 8-14 (4 males, 3 females) |
| III | Acitretin gel | 0.02 (Example 3) | 15-21 (4 males, 3 females) |
| IV | Acitretin gel | 0.05 (Example 4) | 22-28 (4 males, 3 females) |

TABLE 6-continued

Study Design for Acitretin Gel for Rhino Mouse Test

| Groups | Formulation/Treatment Details | Concentration (% w/w) | Animal Numbers & Sex |
|---|---|---|---|
| V | Acitretin gel | 0.10 (Example 5) | 29-35 (4 males, 3 females) |
| VI | Acitretin gel | 0.20 (Example 2) | 36-42 (4 males, 3 females) |
| VII | Tazorac ® (tazarotene) gel | 0.10 | 43-49 (4 males, 3 females) |

After about 72±3 hours following last application (i.e., day 14), all surviving animals were euthanized by cervical dislocation and skin tissue samples (ventral side skin—untreated control site and dorsal side skin—application site) were collected and preserved in 10% neutral buffered formalin for histopathology evaluation. In addition to this, some portion of the dorsal side skin (i.e., application site) from all the animals was also collected in a 0.5% v/v acetic acid solution for whole mount slide preparations and measurement of utriculi diameter.

For whole mount preparations, the skin samples (dorsal side skin, i.e., application site) were cut into approximately 1×1 cm² size and soaked in 0.5% v/v acetic acid solution for approximately 18±1 hours at a temperature of 2° C. to 8° C. The epidermis was carefully peeled off using a flat-ended spatula/blade/fine forceps and placed on a glass slide with the dermal side facing up, and the slides were allowed to air-dry. These tissue slides were later dehydrated by immersing into ascending grades of isopropyl alcohol (75%, 95%, and 100% for approximately 3 minutes to 5 minutes each), followed by xylene, and then mounted. The diameter of at least 10 utriculi (2 utriculi/field) was measured by using a Leica® Application Suite QWin Image Processing and Analysis Software. Mean utricle diameter was calculated for each animal and subjected for group mean comparison by using one way analysis of variance (ANOVA) if complied normality test using D'Agostino-Pearson omnibus. As ANOVA results showed significance, a Dunnett test was applied to compare Group II to Group VII with/over untreated control (Group I) and Group III to Group VII with/over placebo (Group II).

The percentage reduction in utriculi diameter was calculated manually based on mean reduction in the utriculi diameter in different groups with respect to the untreated control (Group I) and placebo (Group II) by using the following formula.

$$\text{Percentage Reduction in utricle diameter} = \frac{\text{Mean Utricle Diameter in Untreated Control or Placebo} - \text{Mean Utricle Diameter in Group } X}{\text{Mean Utricle Diameter in Untreated Control or Placebo}} \times 100$$

wherein "X" is the group for which percentage reduction in utricle diameter was calculated.

Table 7 describes the summary of utriculi size/diameter after application of various strengths of acitretin gels and Tazorac® (tazarotene) gel 0.10% w/w. In the untreated control (Group I) and placebo (Group II) animals, numerous circular-shaped utriculi were noticed in the epidermal sheets (whole mount preparation) with an average diameter of 255.38±37.16 and 233.61±35.41 µm. Application of acitretin gel at all concentrations (0.02% w/w, 0.05% w/w, 0.10% w/w, and 0.20% w/w) produced a significant reduction in the utriculi diameter with an average diameter of 109.52±57.56, 60.30±6.46, 63.64±5.19 and 57.46±5.65 µm in Group III, Group IV, Group V, and Group VI, respectively. Similarly, in Group VII (Tazorac® gel 0.10% w/w), the mean utriculi diameter was reduced up to 45.48±7.33 µm. FIG. 1 shows the mean utriculi size after the application of various strengths of acitretin gel and Tazorac® (tazarotene) gel 0.10% w/w. FIG. 2 shows the percentage reduction in utriculi size after the application of various strengths of acitretin gel and Tazorac® (tazarotene) gel 0.10% w/w with respect to control.

TABLE 7

Summary of Utriculi Size/Diameter

| | Group | | | | | | |
|---|---|---|---|---|---|---|---|
| | I | II | III | IV | V | VI | VII |
| Mean Diameter/Size (in microns) ± SD | 255.38 ± 37.16 | 233.61 ± 35.41 | 109.52**@@ ± 57.56 | 60.30**@@ ± 6.46 | 63.64**@@ ± 5.19 | 57.46**@@ ± 5.65 | 45.48**@@ ± 7.33 |
| N | 7 | 7 | 7 | 7 | 7 | 7 | 7 |
| % Reduction with respect to Control | 0 | 8.53 | 57.12 | 76.39 | 75.08 | 77.50 | 82.19 |
| % Reduction with respect to Placebo | — | 0 | 53.10 | 74.30 | 72.80 | 75.20 | 80.50 |

Group I: Untreated Control
Group II: Placebo for Acitretin Gel - 0%
Group III: Acitretin Gel - 0.02% w/w
Group IV: Acitretin Gel - 0.05% w/w
Group V: Acitretin Gel - 0.10% w/w
Group VI: Acitretin Gel - 0.20% w/w
Group VII: Reference Test Item - Tazorac ® Gel 0.10% w/w.
**Significant at two-sided 1% level of significance; p-value based on Dunnett test for comparing Groups II to VII over Group I (untreated control).
@@Significant at two-sided 1% level of significance; p-value based on Dunnett test for comparing Groups III to VII over Group II (placebo for acitretin gel).

Percentage reduction in utricle diameter with respect to control and placebo has been calculated manually as per given formula and not subjected to statistical analysis.

As compared to control and placebo, application of acitretin gel at all concentrations (0.02% w/w, 0.05% w/w, 0.10% w/w, and 0.20% w/w) significantly reduced the utriculi diameter. The percentage reduction in the utriculi diameter was not much different within different groups, but acitretin gel at and above 0.05% w/w concentration produced comparable and equivalent effects with that of Tazorac® gel 0.10% w/w.

Gross Pathology Studies

At necropsy, mild to moderate scaling was noticed at the application site in some animals in Group IV (4 of 7 animals), Group V (3 of 7 animals), and Group VI (6 of 7 animals). Whereas, in Group VII, 3 of 7 animals were found dead and all dead and moribund sacrificed revealed reddish discoloration and scaling of the skin at the application site. Table 8 presents the summary of gross pathology findings.

TABLE 8

Summary of Gross Pathology Findings

| | Group | | | | | | |
|---|---|---|---|---|---|---|---|
| | I | II | III | IV | V | VI | VII |
| No. of Animals | 7 | 7 | 7 | 7 | 7 | 7 | 7 |
| No. of Dead | 0 | 0 | 0 | 0 | 0 | 0 | 3 |
| External Findings | | | | | | | |
| NAD | 7 | 7 | 7 | 3 | 4 | 1 | 0 |
| Scaling at application site (mild/moderate) | 0 | 0 | 0 | 4 | 3 | 6 | 1 |
| Reddish discoloration and scaling at application site | 0 | 0 | 0 | 0 | 0 | 0 | 6 |

NAD—No Abnormality Detected

Histopathological Studies

Histopathology scores were analyzed by using the Kruskal-Wallis test followed by the Wilcoxon-Mann-Whitney test for comparison of median histologic scores of Group II to VII with/over untreated control (Group I) and those of Group III to VII with/over placebo (Group II—Placebo for Acitretin gel). Further, median histology scores for the ventral side skin (untreated control site) of each group were compared with that of the concurrent dorsal side skin (application site) by using the Wilcoxon signed-rank test. All statistical analyses were performed at 5% level of significance using SAS® Institute's PC SAS 9.1.3.

As compared to untreated control (Group I) and placebo (Group II—placebo for acitretin gel), the severity of dermal inflammation at the site of the application (dorsal side skin) revealed was increased in a concentration-dependent manner as given in Table 9. However, more animals treated with Tazorac® gel (Group VII) showed comparatively higher dermal inflammation than that of acitretin gel treated animals.

TABLE 9

Summary of Histopathology Findings

| | Group | | | | | | |
|---|---|---|---|---|---|---|---|
| | I | II | III | IV | V | VI | VII |
| No. of Animals | 7 | 7 | 7 | 7 | 7 | 7 | 7 |
| No. of Dead | 0 | 0 | 0 | 0 | 0 | 0 | 3 |
| Dermal Changes: Inflammation | | | | | | | |
| Absent (Grade 0) | 6 | 7 | 3 | 1 | 0 | 0 | 1 |
| | (85.7) | (100.0) | (42.9) | (14.3) | (0.0) | (0.0) | (14.3) |
| Minimal (Grade 1) | 1 | 0 | 3 | 3 | 5 | 3 | 2 |
| | (14.3) | (0.0) | (42.9) | (42.9) | (71.4) | (42.9) | (28.6) |
| Mild (Grade 2) | 0 | 0 | 1 | 3 | 2 | 3 | 2 |
| | (0.0) | (0.0) | (14.3) | (42.9) | (28.6) | (42.9) | (28.6) |
| Moderate (Grade 3) | 0 | 0 | 0 | 0 | 0 | 1 | 2 |
| | (0.0) | (0.0) | (0.0) | (0.0) | (0.0) | (14.3) | (28.6) |

Figures in parenthesis indicate percent incidence.

We claim:

1. A stable topical pharmaceutical composition of acitretin comprising a therapeutically effective amount of acitretin from about 0.05% w/w to about 0.2% w/w based on total weight of the composition, a gelling agent, a solvent, and a co-solvent.

2. A stable topical pharmaceutical composition comprising from about 0.05% w/w to about 0.2% w/w of acitretin based on total weight of the composition, wherein more than about 15% of the acitretin is present in a solubilized form.

3. The stable topical pharmaceutical composition of claim 2 comprising about 0.05% w/w of acitretin based on total weight of the composition, wherein about 100% of the acitretin is present in the solubilized form.

4. The stable topical pharmaceutical composition of claim 2 comprising about 0.1% w/w of acitretin based on total weight of the composition, wherein about 70% of the acitretin is present in the solubilized form.

5. The stable topical pharmaceutical composition of claim 2 comprising about 0.2% w/w of acitretin based on total weight of the composition, wherein about 35% of the acitretin is present in the solubilized form.

6. The stable topical pharmaceutical composition of claim 2, wherein the composition is a gel.

7. The stable topical pharmaceutical composition of claim 2, wherein the composition comprises a gelling agent, a solvent, and a co-solvent.

8. The stable topical pharmaceutical composition of claim 1 or 7, wherein the percentage of the gelling agent ranges from about 0.05% w/w to about 10% w/w based on total weight of the composition.

9. The stable topical pharmaceutical composition of claim 1 or 7, wherein the gelling agent is selected from the group comprising carboxyvinyl polymers, natural gums, cellulose derivatives, acrylates, alginic acid-propylene glycol ester, polyoxyethylene-polyoxypropylene copolymers, polyvinyl pyrrolidone, polyethylene glycol, polyethylene oxide, polyvinyl alcohol, silicon dioxide, and mixtures thereof.

10. The stable topical pharmaceutical composition of claim 9, wherein the gelling agent is a carboxyvinyl polymer.

11. The stable topical pharmaceutical composition of claim 1 or 7, wherein the solvent is selected from the group comprising water, white soft paraffin, light liquid paraffin, heavy liquid paraffin, mineral oil, hydrocarbon oil, ester oil, triglyceride oil, oil of plant origin, oil of animal origin, unsaturated or polyunsaturated oil, essential oil, silicone oil, and mixtures thereof.

12. The stable topical pharmaceutical composition of claim 11, wherein the solvent is water.

13. The stable topical pharmaceutical composition of claim 1 or 7, wherein the co-solvent is selected from the group comprising ethers, glycols, dimethyl isosorbide, fatty acid esters, fatty acids, polyoxyethylene sorbitan esters, and mixtures thereof.

14. The stable topical pharmaceutical composition of claim 13, wherein the co-solvent is diethylene glycol monoethyl ether.

15. The stable topical pharmaceutical composition of claim 13, wherein the co-solvent is dimethyl isosorbide.

16. The stable topical pharmaceutical composition of claim 13, wherein the co-solvent is polysorbate 80.

17. The stable topical pharmaceutical composition of claim 13, wherein the co-solvent is a combination of diethylene glycol monoethyl ether, dimethyl isosorbide; and polysorbate 80.

18. The stable topical pharmaceutical composition of claim 17, wherein diethylene glycol monoethyl ether is present in a range of about 20% to about 30% w/w based on total weight of the composition.

19. The stable topical pharmaceutical composition of claim 17, wherein dimethyl isosorbide is present in a range of about 1% to about 10% w/w based on total weight of the composition.

20. The stable topical pharmaceutical composition of claim 17, wherein polysorbate 80 is present in a range of about 0.1% to about 5% w/w based on total weight of the composition.

21. The stable topical pharmaceutical composition of claim 1 or 7, wherein the composition further comprises one or more pharmaceutically acceptable excipients selected from the group comprising percutaneous absorption enhancers, antioxidants, preservatives, chelating agents, surfactants, pH-adjusting agents, humectants, fragrances, and mixtures thereof.

22. The stable topical pharmaceutical composition of claim 1 or 7, wherein the composition has a pH from about 4 to about 7.

23. A stable topical pharmaceutical composition comprising at least about 0.05% w/w of acitretin based on total weight of the composition, wherein the composition has a mean in-vitro release rate of more than about 10.00 $\mu g/cm^2/h^{1/2}$ as measured using a Franz diffusion cell with the conditions of receptor solution comprising isopropyl alcohol and water (60:40, v/v), hydrophilic polyethersulfone (PES) membrane with pore size of 0.2 μm, dosage 300±30 mg, temperature 32° C.±1.0° C.

24. A method of treating a skin disorder by administering the stable topical pharmaceutical composition of claim 1 or 2.

25. The method of treatment of claim 24, wherein the skin disorder is selected from the group comprising psoriasis, keratosis, eczema, rosacea, acne vulgaris, dermatitis, pruritus, seborrhea, skin cancers, inflammation, other skin disorders which are responsive to acitretin or etretinate, and combinations thereof.

26. The method of treatment of claim 25, wherein the skin disorder is psoriasis.

* * * * *